United States Patent
Sund et al.

(10) Patent No.: US 11,903,867 B2
(45) Date of Patent: *Feb. 20, 2024

(54) OSTOMY DEVICE WITH A NONWOVEN ELEMENT COMPRISING A WATER-SOLUBLE COMPONENT AND A RELEASABLE MATERIAL

(71) Applicant: Coloplast A/S, Humlebaek (DK)

(72) Inventors: Anders Grove Sund, Alleroed (DK); Richard Morgan Hickmott, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,446

(22) Filed: Dec. 6, 2022

(65) Prior Publication Data

US 2023/0096159 A1 Mar. 30, 2023

Related U.S. Application Data

(63) Continuation of application No. 16/498,419, filed as application No. PCT/DK2018/050067 on Apr. 9, 2018, now Pat. No. 11,547,598.

(30) Foreign Application Priority Data

Apr. 10, 2017 (DK) ............................ PA 2017 70255

(51) Int. Cl.
| | | |
|---|---|---|
| A61F 5/445 | (2006.01) | |
| A61F 5/443 | (2006.01) | |
| A61F 5/44 | (2006.01) | |
| A61L 24/00 | (2006.01) | |

(52) U.S. Cl.
CPC .............. *A61F 5/445* (2013.01); *A61F 5/443* (2013.01); *A61L 24/0073* (2013.01); *A61F 5/4404* (2013.01); *A61L 2400/14* (2013.01)

(58) Field of Classification Search
CPC ......... A61F 5/443; A61F 5/4404; A61F 5/448
See application file for complete search history.

(56) References Cited

U.S. PATENT DOCUMENTS

| | | | | |
|---|---|---|---|---|
| 3,081,771 | A | * 3/1963 | Lee | A61F 5/443 604/344 |
| 4,710,182 | A | 12/1987 | Bryson | |
| 4,753,703 | A | * 6/1988 | Jensen | A61F 5/443 414/791.2 |

(Continued)

FOREIGN PATENT DOCUMENTS

| | | |
|---|---|---|
| EP | 2080829 A1 | 7/2009 |
| FR | 2659295 A3 | 9/1991 |

(Continued)

*Primary Examiner* — Guy K Townsend
(74) *Attorney, Agent, or Firm* — Coloplast Corp., Coloplast A/S; Nick Baumann

(57) ABSTRACT

An ostomy device includes a nonwoven element having a water-soluble component and a releasable material. When the ostomy device is applied to a user and stomal output contacts the distal surface of the nonwoven element, the water-soluble component dissolves and releases the releasable material from the nonwoven element to neutralize at least one of enzyme activity and pH of the stomal output.

14 Claims, 3 Drawing Sheets

(56) References Cited

U.S. PATENT DOCUMENTS

| | | | |
|---|---|---|---|
| 4,793,337 A * | 12/1988 | Freeman | A61L 15/58 442/151 |
| 4,806,261 A | 2/1989 | Ciallella et al. | |
| 5,051,259 A * | 9/1991 | Olsen | A61F 13/0213 428/355 R |
| 5,074,852 A * | 12/1991 | Castellana | A61F 5/443 604/336 |
| 5,160,654 A | 11/1992 | Falou et al. | |
| 5,591,820 A * | 1/1997 | Kydonieus | A61L 31/148 528/905 |
| 5,714,225 A * | 2/1998 | Hansen | A61F 13/0246 428/114 |
| 5,714,543 A * | 2/1998 | Shah | C08L 29/00 525/123 |
| 5,912,059 A * | 6/1999 | Jones | A61F 5/443 428/35.5 |
| 6,166,117 A | 12/2000 | Miyazaki | |
| 6,482,491 B1 * | 11/2002 | Samuelsen | A61K 9/703 442/151 |
| 6,764,474 B2 * | 7/2004 | Nielsen | A61F 5/448 604/336 |
| 6,869,422 B2 * | 3/2005 | Fenton | A61F 5/445 604/338 |
| 7,347,844 B2 * | 3/2008 | Cline | A61F 5/448 604/338 |
| 7,348,018 B2 | 3/2008 | McAtee et al. | |
| 7,378,360 B2 | 5/2008 | Clark et al. | |
| 7,777,092 B2 * | 8/2010 | Lykke | A61F 13/025 428/343 |
| 7,857,796 B2 * | 12/2010 | Cline | A61F 5/448 604/277 |
| 7,858,836 B2 * | 12/2010 | Sambasivam | A61L 15/40 523/111 |
| 8,277,427 B2 * | 10/2012 | Edvardsen | A61F 5/443 604/355 |
| 8,439,883 B1 * | 5/2013 | Johnsen | A61F 5/448 604/338 |
| 8,979,813 B2 * | 3/2015 | Uveborn | A61F 13/0236 604/338 |
| 9,010,338 B2 * | 4/2015 | Rustemeyer | A01N 25/10 131/345 |
| 9,303,358 B2 * | 4/2016 | Juhl | D21H 17/26 |
| 10,413,440 B2 * | 9/2019 | Moavenian | A61F 5/443 |
| 10,470,936 B2 * | 11/2019 | Wohlgemuth | C09J 123/22 |
| 10,512,562 B2 * | 12/2019 | Kavanagh | A61F 5/448 |
| 11,160,681 B2 * | 11/2021 | Strøbech | A61F 5/445 |
| 11,304,854 B2 * | 4/2022 | Wohlgemuth | A61L 26/008 |
| 11,534,326 B2 * | 12/2022 | Sund | A61F 5/448 |
| 11,547,598 B2 * | 1/2023 | Sund | A61L 24/0073 |
| 11,571,325 B2 * | 2/2023 | Kavanagh | A61F 5/448 |
| 2002/0088080 A1 * | 7/2002 | Fenton | A61F 5/445 604/338 |
| 2003/0045197 A1 | 3/2003 | Kakiuchi et al. | |
| 2004/0185079 A1 | 9/2004 | Zomer | |
| 2004/0193122 A1 * | 9/2004 | Cline | A61F 5/448 604/332 |
| 2004/0223944 A1 * | 11/2004 | Capelli | A61K 47/585 424/618 |
| 2004/0230170 A1 * | 11/2004 | Fenton | A61F 5/445 604/336 |
| 2005/0143697 A1 | 6/2005 | Riesinger | |
| 2005/0247419 A1 | 11/2005 | Hamed et al. | |
| 2006/0141016 A1 * | 6/2006 | Sambasivam | A61P 17/00 424/773 |
| 2007/0179461 A1 * | 8/2007 | Sambasivam | C09J 183/04 604/336 |
| 2008/0119804 A1 * | 5/2008 | Cline | A61F 5/445 604/338 |
| 2008/0275327 A1 * | 11/2008 | Faarbaek | A61B 5/6833 600/382 |
| 2008/0319368 A1 * | 12/2008 | Lykke | A61F 13/025 602/57 |
| 2009/0221047 A1 | 9/2009 | Schindler et al. | |
| 2009/0311307 A1 * | 12/2009 | Lykke | B05D 3/00 424/443 |
| 2010/0168693 A1 * | 7/2010 | Edvardsen | A61F 5/451 604/355 |
| 2010/0318052 A1 * | 12/2010 | Ha | A61F 13/0226 604/385.01 |
| 2011/0213322 A1 * | 9/2011 | Cramer | A61F 5/443 604/332 |
| 2012/0302981 A1 * | 11/2012 | Lam | A61F 5/445 604/338 |
| 2012/0323193 A1 | 12/2012 | Johannison et al. | |
| 2013/0090617 A1 * | 4/2013 | Uveborn | A61F 13/024 604/344 |
| 2013/0123678 A1 * | 5/2013 | Carty | A61F 13/0253 602/54 |
| 2013/0317405 A1 * | 11/2013 | Ha | A61F 13/00 602/42 |
| 2014/0121304 A1 | 5/2014 | Kelly et al. | |
| 2014/0194844 A1 | 7/2014 | Edvardsen et al. | |
| 2014/0316360 A1 | 10/2014 | Ekfeldt et al. | |
| 2015/0018788 A1 * | 1/2015 | Pham | B32B 27/08 428/518 |
| 2015/0073325 A1 * | 3/2015 | Oeelund | A61L 15/225 602/46 |
| 2015/0284597 A1 * | 10/2015 | Carty | C09J 7/255 206/229 |
| 2015/0359656 A1 * | 12/2015 | Hansen | A61F 5/443 604/344 |
| 2016/0235582 A1 * | 8/2016 | Moavenian | A61F 5/448 |
| 2016/0302959 A1 * | 10/2016 | Kavanagh | A61F 5/449 |
| 2017/0095431 A1 * | 4/2017 | Andrews | A61K 31/155 |
| 2018/0071150 A1 * | 3/2018 | Wohlgemuth | C08L 23/18 |
| 2018/0116859 A1 * | 5/2018 | Strøbech | A61F 5/445 |
| 2020/0046541 A1 * | 2/2020 | Sund | A61F 5/445 |
| 2020/0093632 A1 * | 3/2020 | Kavanagh | A61F 5/448 |
| 2022/0008240 A1 * | 1/2022 | Strøbech | A61F 5/445 |

FOREIGN PATENT DOCUMENTS

| | | | |
|---|---|---|---|
| GB | 1256866 A * | 12/1971 | A61F 5/443 |
| GB | 1256866 A | 12/1971 | |
| GB | 2322302 A * | 8/1998 | A61F 5/443 |
| GB | 2322302 A | 8/1998 | |
| JP | 2007197862 A | 8/2007 | |
| JP | 2014133955 A | 7/2014 | |
| WO | 2013053410 A1 | 4/2013 | |
| WO | 2017190752 A1 | 11/2017 | |
| WO | WO-2017190752 A1 * | 11/2017 | A61F 5/445 |

* cited by examiner

OSTOMY DEVICE WITH A NONWOVEN ELEMENT COMPRISING A WATER-SOLUBLE COMPONENT AND A RELEASABLE MATERIAL

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general—and for these ostomists in particular—safe, reliable and efficient ostomy devices are highly desirable. Numerous attempts have been made to provide ostomy devices to meet such requirements, e.g. the requirement of prolonged wear time, but the provision of sufficient efficiency to achieve a satisfactory long wear time of ostomy devices continues to be an unmet need.

Ostomists and health care professionals alike would welcome improvements in ostomy devices to better meet such requirements.

SUMMARY

The present disclosure provides aspects of a body side member of an ostomy appliance according to the appended claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
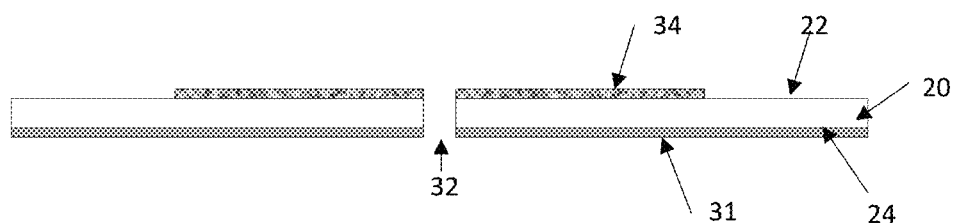
FIG. 1A is a schematic, cross-section side view of one embodiment of a body side member of an ostomy appliance.

In the following detailed description, reference is made to the accompanying drawings, which form a part hereof, and in which is shown by way of illustration specific embodiments in which the invention may be practiced. In this regard, directional terminology, such as "top", "bottom", "front", "back", "leading", "trailing", etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output", "waste(s)", and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

Moreover, "releasable material" should be interpreted to include a sacrificial component of the body side member, i.e. a material suitable for being "sacrificed" to avoid or slow the breaking down of the adhesive of the body side member and/or any of the other components of the body side member.

The use of the phrase "substantially" as a qualifier of certain features or effects in this disclosure, is intended to simply mean that any deviations are within tolerances that would normally be expected by the skilled person in the relevant field.

In one aspect, the present disclosure relates to a body side member of an ostomy appliance comprising a proximal surface and a distal surface. At least a portion of the proximal surface comprises an adhesive. The body side member comprises a centre portion. At least the centre portion is prepared for the provision of a stoma receiving opening extending through the body side member. The body side member includes a nonwoven element forming at least a portion of the distal surface.

The nonwoven element of the body side member comprises a releasable material. The nonwoven element is configured such that—on contact of the nonwoven element with liquid—the releasable material is released from the nonwoven element. Typically, such functionality is achieved by one or more components of the nonwoven element being at least partially water-soluble, The liquid which contacts the nonwoven element is stomal output, which contains water as a primary component.

Release of the releasable material may take place onto the distal surface of the body side member, at least in use of the body side member around a stoma of a user. "At least in use" should be interpreted such that, as long as the body side member is not prepared for, or attached to, the skin surface of a user, the releasable material is not intended to be released onto the distal surface of the body side member.

The proximal surface of the body side member comprises an adhesive. In embodiments, the adhesive comprises a plurality of different adhesive materials. In one embodiment, the different adhesive materials of the adhesive are provided in a side-by-side manner. In one embodiment, the different adhesive materials of the adhesive are provided as a layered structure. In one embodiment, the different adhesive materials of the adhesive are provided primarily side-by-side, but with some overlapping portions of the different adhesive materials. Examples of suitable adhesive materials are given below.

The releasable material is provided inter alia to provide a better neutralising effect of stomal fluids. Thereby stomal fluids, which often contain very aggressive bodily substances (e.g. including certain enzymes produced in the body), are neutralised before they can reach the polymeric matrix of the adhesive on the proximal surface of the device or the peristomal skin. Neutralisation includes both pH neutralisation, e.g. to a pH between 5 and 8, and/or neutralisation of enzyme activity. This in turn helps to avoid both damage to the skin surface (caused by the aggressive stomal fluids), and disintegration and/or failure of the adhesive.

One way in which the body side member of the present disclosure allows for an improved neutralising effect, is by allowing the releasable material to be released from the nonwoven element and come into contact with stomal output.

The nonwoven element forms at least a portion of the distal surface of the body side member. In embodiments, the nonwoven element is configured to provide or define an entirety of the distal surface of the body side member, including the centre portion. In other embodiments, the nonwoven element can be configured to extend over and cover only a portion of the distal surface, i.e. configured such that it only extends over a portion of a radial distance between the centre portion and/or the stoma receiving opening and an outermost edge or outermost edge portion of the body side member. In one aspect, the nonwoven element may be in two separate parts (i.e. with no fluid connectivity between the two parts); one part which is arranged such that it lies below the stomal opening when the user is standing up, and another part which is arranged on the opposite side of the stomal opening.

The nonwoven element comprises a releasable material. A "releasable material" is on which is released from the nonwoven element upon contact of said nonwoven element with liquid, such as stomal exudate.

In one aspect, one or more components of the nonwoven element are configured to be at least partially water-soluble. In this manner, on contact of the nonwoven element with liquid, the structure nonwoven element at least partially degrades, and releasable material is released from the nonwoven element. In one aspect, the nonwoven element itself degrades, releasing fibres in addition to the releasable material. Alternatively, releasable material can be released from the nonwoven element upon contact with liquid, without significant degradation of the nonwoven element.

In embodiments, the nonwoven element comprises one or more fibrous layers. By varying the arrangement of layers, a variation in the release profile of the releasable material can be achieved, and a nonwoven element can be tailored to suit the particular chemistry of a particular stomal exudate.

In embodiments, the nonwoven element comprises hydrophilic fibres, and optionally hydrophobic fibres. Suitably, the nonwoven element comprises both hydrophilic and hydrophobic fibres. The correct balance of hydrophilic and hydrophobic fibres can lead to the correct release profile of the releasable material. Fibres which are hydrophilic in nature may be coated to as to make them hydrophobic, and vice-versa.

In an embodiment, the nonwoven element comprises a water-soluble binder. The water-soluble binder acts to maintain the structure of the nonwoven element prior to contact with liquid, but dissolves in water so that the nonwoven element degrades. The water-soluble binder may itself comprise fibres. In an aspect, the fibres of the nonwoven element are water-soluble; in this manner, the effects of a binder are complemented by the fibres, and a binder may even be avoided.

In one embodiment, the releasable material is integrated in the structure of the nonwoven element. In a further embodiment, the releasable material is integrated in the structure of the nonwoven element such that release of the releasable material prior to contact with liquid is minimal, or even absent. In this manner, the releasable material is only released when needed.

In an embodiment, the content of releasable material in the nonwoven element is at least 20% w/w, such as at least 30% w/w, at least 40% w/w or at least 45% w/w. Such a content of releasable material is relatively high, meaning that a high concentration of releasable material can be achieved adjacent the stoma.

In embodiments, the releasable material is in the form of a powder or fibres. These options each provides one or more different advantages including, but not limited to, manipulability, shelf life, suitability for different kinds of stomal output (colostomy output tends to be more solid than ileo- and urostomy output), processing characteristics and others. By selectively applying these options, individually or in combination, to meet particular requirements of a target ostomy group, the suitability of the appliance and the improvement in neutralising effect, can be significantly enhanced.

In aspects, the releasable material is a neutralising substance, e.g. an enzyme neutralizing substance or a pH neutralising substance, preferably an enzyme neutralising substance.

By neutralizing substance is herein meant a substance capable of neutralizing or at least minimizing the level of skin- or adhesive-aggressiveness of the output. In some embodiments, the releasable material is a mineral material. The releasable material may comprise a plurality of different materials, so that the properties with respect to e.g. neutralisation can be tailored.

In embodiments, the neutralizer comprises a clay, such as organophilic clay, for example bentonite or synthetic clay such as laponite. In embodiments, the neutralizing substance may be potato-derived inhibitors or protease inhibitors. Examples of potato-derived inhibitors such as potato protein is disclosed in EP 1 736 136.

The nonwoven element typically takes the form of a layer or layers of nonwoven material comprising releasable material. Releasable material may be present in a given nonwoven layer of the nonwoven element. Alternatively or additionally, releasable material may be present between nonwoven layers. The nonwoven element is formed through nonwoven laying techniques, such as airlaying, wet-laying or spinning. Release material can be incorporated in such techniques as required. The nonwoven element and/or the individual nonwoven layers can be processed by e.g. interlacing, tangling, heat treatment or embossing etc.

In aspects, the nonwoven element is formed as an integral component of the body side member. Alternatively, the nonwoven element is formed as a separate component and is configured to be attachable to other components of the body side member. This allows a nonwoven element—once used—to be replaced without replacing the entire body side element. The nonwoven element typically has a thickness of between 1-5 mm, a diameter between 3-10 cm and a substantially circular, square or oval shape in the plane of the body side plate. Edges or the nonwoven element may be rounded as required.

In embodiments, at least a centre portion of the nonwoven element comprises a stoma-receiving opening, or is prepared for provision of a stoma-receiving opening extending through the nonwoven element. In this manner, the user can select the size and shape of the opening in the nonwoven element which provides the best functionality (e.g. the best fit). In a particular embodiment, regions of the nonwoven element may comprise no releasable material, and be designed to be cut or punched out by a user, thereby "activating" the nonwoven element. In one aspect of this embodiment, the central region of the nonwoven element, being that region which is to receive a stoma, does not comprise releasable material. This region can be cut out by a user. Alternatively, the central region of the nonwoven element may disintegrate in water, forming an opening in the nonwoven element. In this manner, releasable material is not wasted when the central region is removed. One way of achieving such functionality is by welding or otherwise connecting the uppermost and lowermost layers of the nonwoven element to each other in the regions of interest.

In embodiments, an additional layer comprising releasable material is located between the nonwoven element and the body side member. On contact of the nonwoven element with liquid, the releasable material is released from the additional layer. The additional layer therefore acts as a reservoir which can provide a release profile of releasable material which is different to that of the nonwoven element. For instance, the nonwoven element can provide an initial "pulse" of releasable material, while the additional layer can provide a "steady state" release of releasable material. Alternatively, the nonwoven element can provide a "steady state" release of releasable material, and the additional layer provides a "pulse" of releasable material. Such an additional layer may be in the form of a gel or paste which comprises releasable material.

Experience shows that when an innermost edge portion of the body side member, or the centre portion of the body side member immediately adjacent to, or surrounding the stoma receiving opening, is engaged ("attacked") by aggressive stomal fluids, it may often cause a surprisingly (fast) breakdown of the adhesive of the proximal surface of the body side member starting from that innermost edge portion and egressing radially therefrom. This may in turn lead to failure of the adhesive, thus rendering the body side member and/or the whole ostomy appliance useless. Prior solutions have focussed on addressing such problems at the area of a body side member immediately adjacent to the stoma, i.e. have tried to solve the issues at the innermost edge portion of the body side member.

Contrary to this, the present disclosure provides different and inventive solutions to overcome these and other problems, because at least in some approaches, the problems are believed to be mitigated or reduced wholly or partly, because of the better options for distributing how and where the releasable material egress out of the nonwoven element. By way of example, but not exclusively, this is achieved by distributing or "spreading" the releasable material over a larger or even all the distal surface of the body side member.

The releasable material can be released in an axial direction (such that the releasable material enters onto the distal surface of the body side member) or in a radial direction (i.e. towards the stoma's surface) immediately adjacent the stoma. In this regard, one or more foils (e.g. plastic films) may be located at the distal surface of the nonwoven element, to direct release of releasable material. One or more foils (e.g. plastic films) may also be located at the proximal surface of the nonwoven element, to direct release of releasable material.

In one embodiment, the body side member further comprises a reinforcing element. The reinforcing element may particularly, but not exclusively, include a sheet or layer of a polymeric film material, such as polyethylene (PE) or polypropylene (PP). Other film materials having additional characteristics, e.g. higher/lower liquid-, vapor- or gas-impermeability or odour control and others, may additionally and/or alternatively be used. Other reinforcing element options include mesh or mesh-shaped and/or woven materials. In one embodiment, the reinforcing element can be located between the adhesive on the proximal surface and the cover layer. In one embodiment, the reinforcing element can be embedded (contained completely) in the adhesive of the proximal surface of the body side member. In one embodiment, the reinforcing element includes reinforcing fibres.

One advantageous effect of the reinforcing element is that it helps provide a body side member which is more resistant to forces acting on it. Often a stoma is located on the lower portion of the abdomen of the user (corresponding to the location of the intestines). Thus, some examples of forces acting on the body side member include forces generated by the clothes of the user, such as at the waist lining of a pair of pants or jeans, such forces often further amplified by the presence of a belt. The forces may be both pressure and shear forces, often in combination.

In embodiments, the nonwoven element comprises a differentiated thickness when viewed over a total extent of the nonwoven element. In one embodiment, a thickness of the nonwoven element decreases from a greater thickness at an outermost edge portion of the nonwoven element to be thinner radially closer to the centre portion of the body side member. The differentiated thickness of the nonwoven element is believed to be useful in providing a smooth egression of the releasable material from the nonwoven element.

In embodiments, the nonwoven element forms the distal surface of the body side member. In embodiments, a proximal surface of the nonwoven element, comprises an adhesive providing the adhesive of the proximal surface of the body side member.

Pressure sensitive adhesives, particularly those containing hydrocolloids, is a particularly suitable group of adhesives being characterized by having a particulate phase of hydrocolloids dispersed in the adhesive phase or matrix. Adhesive containing hydrocolloids may absorb moisture from the skin avoid occlusion of the skin, while maintaining its adhesive properties to skin. Moreover, and adhesive body containing hydrocolloids may have any thickness and still having the non-occlusive properties. A hydrocolloid adhesive may be processed as a hot melt and is easily moulded into specific shapes.

A typical pressure sensitive adhesive composition comprises a substantially homogeneous mixture of 10-60 weight percent of one or more rubbery elastomeric components, 5-60% of one or more absorbent particles, 0-50% tackifier resin, 0-10% of a plasticiser and 0-60% of a non-polar oily extender, based on the total weight of the composition. The rubbery elastomeric base could be selected from the group consisting of physically cross-linked elastomers (suitably block copolymers containing polystyrene blocks), a chemically cross-linked natural or synthetic rubbery elastomer, or a rubbery homopolymer. A physically cross-linked elastomer selected from block-copolymers of styrene, and one or more butadienes may be a styrene-butadiene-styrene block copolymer, a styrene-isoprene copolymer and is preferably a mixture of styrene-isoprene-styrene and styrene-isoprene block copolymers. A chemically cross-linked rubbery elastomer may be e.g. butyl rubber or natural rubber. A rubbery homopolymer may be a polymer of a lower alkene such as low density polyethylene or propylene, preferably atactic polypropylene or polyisobutylene. A tackifying resin optionally used in accordance with the invention is preferably a hydrogenated tackifier resin and is more preferred selected from a group comprising polymers and copolymers of cyclopentadiene, dicyclopentadiene, alpha-pinene or beta-pinene. When the physically cross-linked elastomer is a styrene-butadiene-styrene block copolymer or a styrene-isoprene-styrene block copolymer, the adhesive suitably comprises 0-10% of a plasticiser (e.g. CITROFOL® BII, Jungbunzlauer, Switzerland). The hydrocolloid particles preferably consist of one or more water-soluble or water swelling hydrocolloid polymers or gums. In other embodiments, the adhesive of the proximal surface of the body side member comprises one or more adhesives of the types disclosed in publications WO2007/082538 and WO2009/006901.

In one exemplary implementation and application of the body side member according to the present disclosure, a user initially customizes, such as by cutting, a stoma-receiving opening to an approximate size or circumference of the user's individual stoma. Next, the user can remove any protective liner(s) provided on the body side member, such as on the adhesive of the proximal surface of the body side member and apply the body side member to the skin surface around the stoma. The user can then include the nonwoven element as required in the body side member.

Other helpful effects are envisioned by the body side member according to the disclosure, some of which effects are believed to be at least partly controllable by the composition of the releasable material. In embodiments, more than one kind of releasable material can be provided, thereby allowing for different releasable materials to be released with different release profiles. Thereby, it is believed that more than one helpful effect can be achieved by the claimed body side member. Even further, as an example, in embodiments wherein more than one kind of releasable material is provided in one or more openings of the body side member, the helpful effect(s) presented by one releasable material may be amplified by the presence of another kind of releasable material to provide even better results in terms of reduction or elimination of leakage incidents.

In embodiments, nonwoven element is in the form of an annular disc extending in the plane of the body side member. In aspects, the distal surface of the body side member comprises a first half of a coupling interface for coupling the body side member to a stomal output collecting bag. In one embodiment, the coupling half is a flange adapted to provide a surface for attaching another coupling half in the form of an adhesive flange provided on a stomal output collecting bag. In embodiments, the first half of the coupling interface is configured as a flexible, planar annular flange optionally comprising an adhesive. The first coupling half is adapted to couple with a second coupling half provided around an inlet opening of a stomal output collecting bag by means of an adhesive. The adhesive coupling may provide a releasable or a permanent adhesive coupling engagement between the components. In aspects, the nonwoven element is arranged within said annular ring of the body side member.

In embodiments, the coupling half is an annular ring comprising an upstanding flange protruding from the distal surface perpendicular thereto for attaching another coupling half in the form of a coupling ring provided on a stomal output collecting bag. In one embodiment, a first coupling half is attached to the distal surface of the body side member. In embodiments, the first coupling half is attached to the distal surface by an adhesive or by welding, but other ways of attaching are acceptable. In embodiments, a first coupling half is attached to the distal surface of the body side member at a location radially closer to the stoma-receiving opening than where one or more openings are located.

In embodiments, the distal surface of the body side member comprises one single opening. One single opening should be interpreted to mean one and only one opening. Among other advantages, this provides for a body side member to be produced involving less complicated production steps.

In embodiments, the single opening is configured to extend annularly around the centre portion of the body side member. Among other advantages, these embodiments are particularly suitable for a relatively simple production process.

In embodiments, the first coupling half is configured as an annular ring including an upstanding flange extending axially away from the distal surface of body side member. In one embodiment, the upstanding flange is configured to be perpendicular to the distal surface of the body side member. In one embodiment, the single opening defines an outer perimeter that defines a first, outer diameter D1 being greater than a second, maximum outer diameter D2 of the annular ring forming the first half of the coupling interface.

In one embodiment, the first half of the coupling interface comprises an upstanding flange extending axially away from the distal surface of the body side member. In one embodiment, the upstanding flange is configured to be perpendicular to the distal surface of the body side member. In one embodiment, the upstanding flange forms an annular ring.

In another aspect, the disclosure relates to an ostomy appliance including a body side member as described herein and a stomal output collecting bag. The collecting bag may be configured to be attached to the distal surface of the body side member.

In one embodiment, the ostomy appliance is a one-piece ostomy appliance, i.e. without a coupling interface between the body side member and the stomal output collecting bag. In another embodiment, the ostomy appliance is a two-piece appliance including a coupling interface for connecting a stomal output collecting bag to the body side member by connecting or coupling first and second coupling halves to each other.

In one embodiment, the stomal output collecting bag comprises a second half of a coupling interface that is configured to couple with a first half of the coupling interface on the body side member to attach the stomal collecting bag to the body side member.

In another aspect of the disclosure, use of the body side member for an ostomy appliance as disclosed herein for reducing the frequency of stomal output leakage incidents is further contemplated. The advantageous effects provided by the embodiments of the body side member, aid in alleviating the nuisances of output leakages often encountered by users of ostomy appliances. This is at least partly achieved by the neutralising effects of the releasable material on enzymatic activity or pH of stomal exudate. At the very least, use of the body side member according to the present disclosure allows for an increased wear time of an ostomy appliance and/or reduced irritation of the peristomal skin by stomal exudate.

DETAILED DESCRIPTION OF THE DRAWINGS

FIG. 1A is a cross-sectional side view of one embodiment of a body side member 20 of an ostomy appliance according to the present disclosure. The body side member 20 includes a distal surface 22 ("overside" in FIG. 1A) and a proximal surface 24 ("underside" in FIG. 1A). At least a portion of the proximal surface 24 of the body side member 20 comprises an adhesive 31. FIG. 1A shows a centre portion 28 of the body side member 20 which has been provided with a stoma receiving opening 32. The stoma receiving opening 32 may be provided during manufacture of the body side member 20, or it may be provided by the user in preparing the body side member 20 for attachment to the skin surface around his or her stoma.

Moreover, FIG. 1A shows how the distal surface 22 of the body side member 20 comprises a nonwoven element 34.

In the illustrated embodiment, the nonwoven element 34 is essentially ring-shaped. The illustrated nonwoven element 34 therefore also comprises a stoma receiving opening.

Figure 1B:
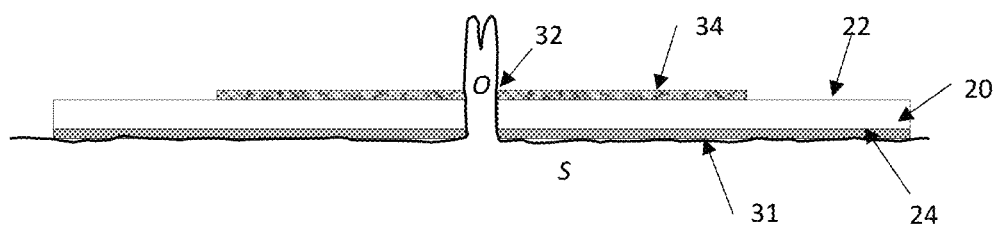
FIG. 1B is a schematic cross-sectional side view of the embodiment of FIG. 1, illustrating the body side member attached to the skin surface of a user.

FIG. 1B is a schematic cross-sectional view illustrating a portion of the body side member 20 of FIG. 1A in place on the skin surface S around a stoma O of a user. The body side member 20 is adhered to a peristomal area of the skin surface S by the adhesive 31.

Figure 1C:
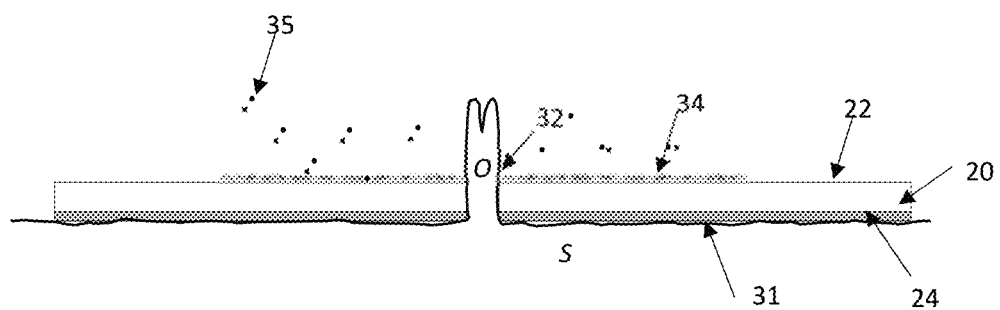
FIG. 1C is a schematic cross-sectional side view of the embodiment of FIG. 1A, illustrating release of releasable material on contact with liquid.

FIG. 1C illustrates the embodiment of FIG. 1A, in which releasable material 35 is released from the nonwoven element 34 upon contact of the nonwoven element with liquid.

Figure 2:
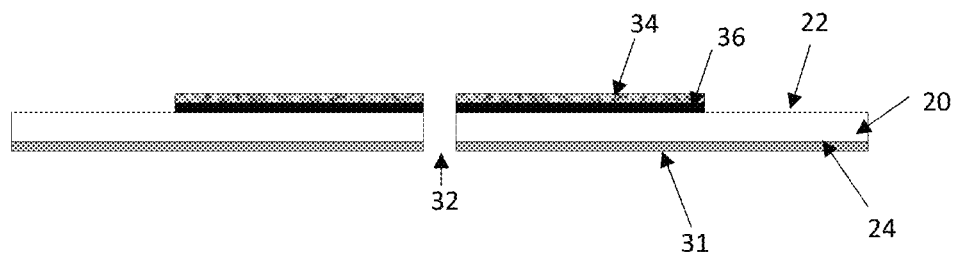
FIG. 2 is a schematic cross-section side view of another embodiment of a body side member of an ostomy appliance.

FIG. 2 is a schematic cross-sectional view of another embodiment of the central region of body side member 20. In this embodiment, an additional layer 36 is present between the nonwoven element 34 and the body side member 20.

Figure 3:
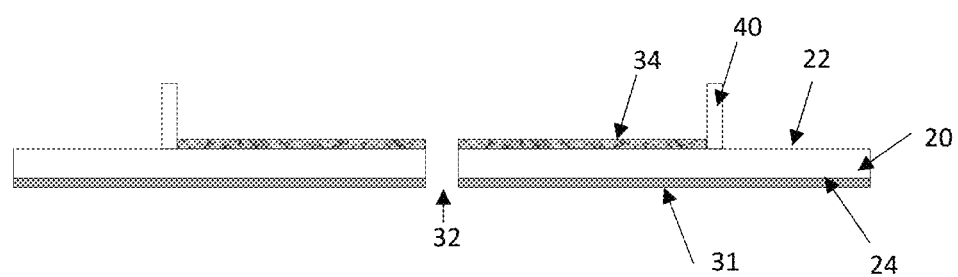
FIG. 3 is a schematic cross-section side view of another embodiment of a body side member of an ostomy appliance.

FIG. 3 is a schematic cross-sectional view of another embodiment of the central region of body side member 20. In this embodiment, the nonwoven element occupies the entirety of the distal surface 22 of the body side member 20 between the opening 32 and a first half 40 of a coupling interface (flange). The illustrated nonwoven element 34 therefore also comprises a stoma receiving opening.

Figure 4:
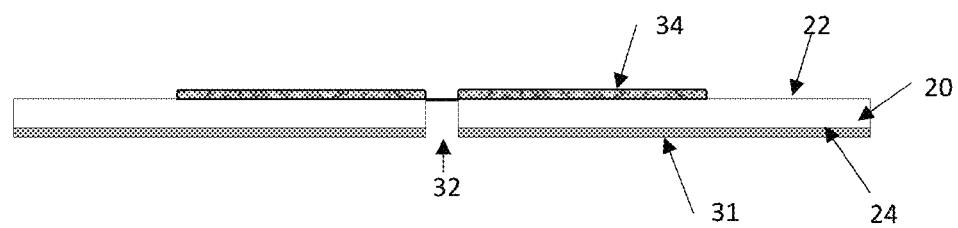
FIG. 4 is a schematic cross-section side view of another embodiment of a body side member of an ostomy appliance.

FIG. 4 is a schematic cross-sectional view of another embodiment of the central region of body side member 20. In this embodiment, the central region of the nonwoven element 34, being that region which is to receive a stoma, does not comprise releasable material. The central region is designed to be removed by a user prior to use of the body side member 20.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. In particular, the illustrated embodiments show two-part ostomy appliances, but the present embodiments can also be used in connection with one-part ostomy appliances. Therefore, it is intended that this invention be limited only by the claims and the equivalents thereof.

The invention claimed is:

1. An ostomy device comprising:
   a nonwoven element having a proximal surface and a distal surface;
   an adhesive applied to the proximal surface of the nonwoven element; and
   a stoma-receiving opening formed through the nonwoven element;
   wherein the nonwoven element comprises a water-soluble component and a releasable material;
   wherein, when the ostomy device is applied to a user and stomal output contacts the distal surface of the nonwoven element, the water-soluble component dissolves and releases the releasable material from the nonwoven element to neutralize at least one of enzyme activity and pH of the stomal output.

2. The ostomy device of claim 1, further comprising:
   a body side member adapted to be coupled to the nonwoven element, where a distal surface of the body side member comprises a coupling interface for attachment with a waste collecting bag.

3. The ostomy device of claim 2, wherein the adhesive on the proximal surface of the nonwoven element is adapted to couple the body side member to skin of the user.

4. The ostomy device of claim 2, wherein, when the body side member is coupled to the nonwoven element, the distal surface of the body side member comprises the distal surface of the nonwoven element.

5. The ostomy device of claim 1, wherein the adhesive applied to the proximal surface of the nonwoven element is adapted to secure the nonwoven element to skin of a user.

6. The ostomy device of claim 1, wherein the nonwoven element comprises more than one fibrous layer.

7. The ostomy device of claim 1, wherein the nonwoven element comprises both hydrophilic fibers and hydrophobic fibers.

8. The ostomy device of claim 1, wherein the nonwoven element comprises water-soluble fibers.

9. The ostomy device of claim 1, wherein the nonwoven element comprises a differentiated thickness wherein a thickness of the nonwoven element measured at an outermost edge portion of the nonwoven element is thicker than a thickness of the nonwoven element measured at the stoma-receiving opening formed through the nonwoven element.

10. The ostomy device of claim 1, wherein a weight content of the releasable material in the nonwoven element is in a range of 20% w/w to 45% w/w.

11. The ostomy device of claim 1, wherein the nonwoven element comprises a water-soluble binder.

12. The ostomy device of claim 1, wherein the releasable material is a clay.

13. The ostomy device of claim 1, wherein the releasable material is a laponite clay.

14. The ostomy device of claim 1, wherein the releasable material is a potato-derived protease enzyme inhibitor.

* * * * *